(12) United States Patent
Shah et al.

(10) Patent No.: US 7,765,489 B1
(45) Date of Patent: Jul. 27, 2010

(54) PRESENTING NOTIFICATIONS RELATED TO A MEDICAL STUDY ON A TOOLBAR

(76) Inventors: Shalin N. Shah, 6980 Woodglen Dr., Hughesville, MD (US) 20637; Nayan Shah, 6980 Woodglen Dr., Hughesville, MD (US) 20637

(*) Notice: Subject to any disclaimer, the term of this patent is extended or adjusted under 35 U.S.C. 154(b) by 0 days.

(21) Appl. No.: 12/558,821

(22) Filed: Sep. 14, 2009

Related U.S. Application Data

(63) Continuation of application No. 12/397,165, filed on Mar. 3, 2009, now abandoned.

(60) Provisional application No. 61/033,391, filed on Mar. 3, 2008.

(51) Int. Cl.
*G06F 3/048* (2006.01)
*G06F 3/00* (2006.01)

(52) U.S. Cl. .............. 715/805; 715/210; 715/760; 715/762; 715/765; 715/772; 715/820

(58) Field of Classification Search ............ 715/210, 715/760, 762, 765, 772, 805, 810
See application file for complete search history.

(56) References Cited

U.S. PATENT DOCUMENTS

| | | | | |
|---|---|---|---|---|
| 5,588,105 A * | 12/1996 | Foster et al. | ............... | 715/779 |
| 5,917,491 A * | 6/1999 | Bauersfeld | ............... | 715/810 |
| 6,072,486 A * | 6/2000 | Sheldon et al. | ............... | 715/835 |
| 6,119,098 A * | 9/2000 | Guyot et al. | ............... | 705/14.61 |
| 6,226,655 B1 * | 5/2001 | Borman et al. | ............... | 715/207 |
| 6,232,972 B1 * | 5/2001 | Arcuri et al. | ............... | 715/815 |
| 6,624,831 B1 * | 9/2003 | Shahine et al. | ............... | 715/815 |
| 6,820,235 B1 | 11/2004 | Bleicher et al. | | |
| 6,878,112 B2 * | 4/2005 | Linberg et al. | ............... | 600/300 |
| 7,120,865 B1 * | 10/2006 | Horvitz et al. | ............... | 715/210 |
| 7,340,503 B2 * | 3/2008 | Washburn | ............... | 709/206 |
| 7,376,902 B2 * | 5/2008 | Lueckhoff | ............... | 715/752 |
| 7,412,655 B2 * | 8/2008 | Wada et al. | ............... | 715/744 |
| 7,536,652 B2 * | 5/2009 | Uemura et al. | ............... | 715/805 |
| 2002/0016719 A1 * | 2/2002 | Nemeth et al. | ............... | 705/2 |
| 2002/0042723 A1 | 4/2002 | Rice et al. | | |
| 2002/0052890 A1 * | 5/2002 | Ingram et al. | ............... | 707/500.1 |
| 2002/0070969 A1 * | 6/2002 | Barksdale et al. | ............... | 345/765 |
| 2002/0165852 A1 * | 11/2002 | Gogolak | ............... | 707/3 |

(Continued)

FOREIGN PATENT DOCUMENTS

WO 01/45774 6/2001

OTHER PUBLICATIONS

Lambadaris, I. et al. "A study and proposal for Public Alert System using the Internet" Jun. 24, 2003.*

(Continued)

*Primary Examiner*—Steven B Theriault
(74) *Attorney, Agent, or Firm*—Fish & Richardson P.C.

(57) ABSTRACT

Participants of a medical study are notified of and perceive information related to adverse events on a toolbar. The configuration of a toolbar may be different if a serious adverse event is being presented than if an insignificant adverse event is being presented. Serious adverse events include adverse events having severity greater than insignificant adverse events, having severity greater than a predetermined threshold, requiring hospitalization, and/or being life-threatening. Insignificant adverse events include adverse events that affect patients in an unexpected manner.

14 Claims, 16 Drawing Sheets

U.S. PATENT DOCUMENTS

| | | | |
|---|---|---|---|
| 2002/0186257 A1* | 12/2002 | Cadiz et al. | 345/838 |
| 2002/0188474 A1 | 12/2002 | Collamore et al. | |
| 2003/0011646 A1* | 1/2003 | Levine et al. | 345/848 |
| 2003/0046401 A1* | 3/2003 | Abbott et al. | 709/228 |
| 2003/0164862 A1* | 9/2003 | Cadiz et al. | 345/838 |
| 2003/0174154 A1* | 9/2003 | Yukie et al. | 345/700 |
| 2003/0184582 A1* | 10/2003 | Cohen | 345/736 |
| 2003/0195811 A1* | 10/2003 | Hayes et al. | 705/26 |
| 2003/0214534 A1* | 11/2003 | Uemura et al. | 345/805 |
| 2004/0010418 A1* | 1/2004 | Buonocore et al. | 705/2 |
| 2004/0061720 A1* | 4/2004 | Weber | 345/760 |
| 2004/0082345 A1* | 4/2004 | Lueckhoff | 455/456.3 |
| 2004/0093238 A1* | 5/2004 | Deakter | 705/2 |
| 2004/0093240 A1* | 5/2004 | Shah | 705/2 |
| 2004/0122701 A1 | 6/2004 | Dahlin et al. | |
| 2005/0004814 A1* | 1/2005 | Seltzer | 705/2 |
| 2005/0039141 A1* | 2/2005 | Burke et al. | 715/810 |
| 2005/0039144 A1* | 2/2005 | Wada et al. | 715/840 |
| 2005/0075544 A1 | 4/2005 | Shapiro et al. | |
| 2005/0149852 A1 | 7/2005 | Bleicher et al. | |
| 2005/0198220 A1* | 9/2005 | Wada et al. | 709/220 |
| 2005/0246658 A1* | 11/2005 | Uemura et al. | 715/805 |
| 2005/0278651 A1* | 12/2005 | Coe et al. | 715/779 |
| 2006/0059136 A1* | 3/2006 | Wooldridge et al. | 707/3 |
| 2006/0085758 A1* | 4/2006 | Backus | 715/772 |
| 2006/0095860 A1* | 5/2006 | Wada et al. | 715/771 |
| 2006/0149597 A1* | 7/2006 | Powell et al. | 705/2 |
| 2006/0168043 A1* | 7/2006 | Eisenberger et al. | 709/206 |
| 2006/0224326 A1* | 10/2006 | St. Ores et al. | 702/19 |
| 2006/0272652 A1* | 12/2006 | Stocker et al. | 128/898 |
| 2007/0047701 A1* | 3/2007 | Morris | 379/100.08 |
| 2007/0143691 A1* | 6/2007 | Abraham-Fuchs et al. | 715/751 |
| 2007/0168451 A1 | 7/2007 | Taylor et al. | |
| 2007/0180381 A1* | 8/2007 | Rice et al. | 715/711 |
| 2007/0226175 A1 | 9/2007 | Resnic et al. | |
| 2007/0255584 A1 | 11/2007 | Pavlatos et al. | |
| 2008/0004502 A1 | 1/2008 | Ash et al. | |
| 2008/0010088 A1* | 1/2008 | Ben-Attar et al. | 705/2 |
| 2008/0046469 A1 | 2/2008 | Ikeguchi et al. | |
| 2008/0059241 A1* | 3/2008 | Zahlmann et al. | 705/3 |
| 2008/0134084 A1 | 6/2008 | Clark et al. | |
| 2008/0172382 A1* | 7/2008 | Prettejohn | 707/6 |
| 2008/0201171 A1* | 8/2008 | Brushwood | 705/2 |
| 2008/0256128 A1* | 10/2008 | Pierce et al. | 707/104.1 |
| 2009/0083661 A1* | 3/2009 | Blinnikka et al. | 715/787 |
| 2009/0144723 A1* | 6/2009 | Hartin et al. | 717/173 |
| 2009/0158211 A1* | 6/2009 | Gogolak | 715/811 |
| 2009/0164922 A1* | 6/2009 | Phakousonh et al. | 715/762 |
| 2009/0216555 A1* | 8/2009 | Mitchell et al. | 705/3 |

OTHER PUBLICATIONS

Georganas et al., "A Multimedia Communications System for Medical Applications," IEEE International Conference on Communications, vol. 3, Jun. 1989, pp. 1496-1500.

Van Dantzich et al., "Scope: Providing awareness of multiple notifications at a glance," Proceedings of Advanced Visual Interfaces (AVI 2002), accessed Oct 1, 2008, available at research.microsoft.com/~marycz/scope.pdf.

MAS (Member Activity Summary) Toolbar, accessed Oct. 1, 2008, available at http://www.bcbs.com/innovations/blueworks/provider/mas-member-activity-summary.html.

Tate et al., "Development of an Effective User Interface for a Computerized Laboratory Alerting System," Proceedings of the Sixth Annual IEEE Symposium on Computer-Based Medical Systems, Jun. 1993, pp. 183-188.

\* cited by examiner

150

Medical Messenger

Survey Template

1. Do you currently participate in Clinical Trials?
   ○ Yes
   ○ No

2. If no, would you like to be an investigator in Clinical Trials?
   ○ Yes
   ○ No 3. Your area of interest in Oncology:
   ☐ Leukemia           ☐ Colon Cancer
   ☐ Breast Cancer      ☐ Prostate Cancer
   ☐ Lung Cancer        ☐ Other 4. Type of Practice:
   ○ Solo Practice      ○ University Affiliated
   ○ Group Practice     ○ Academic Researcher 5. Have you worked with Central IRB?
   ○ Yes
   ○ No 6. Does your practice have its own Infusion Center?
   ○ Yes
   ○ No 160 →
170 →
180 → Submit
190 → Exit

FIG. 1b

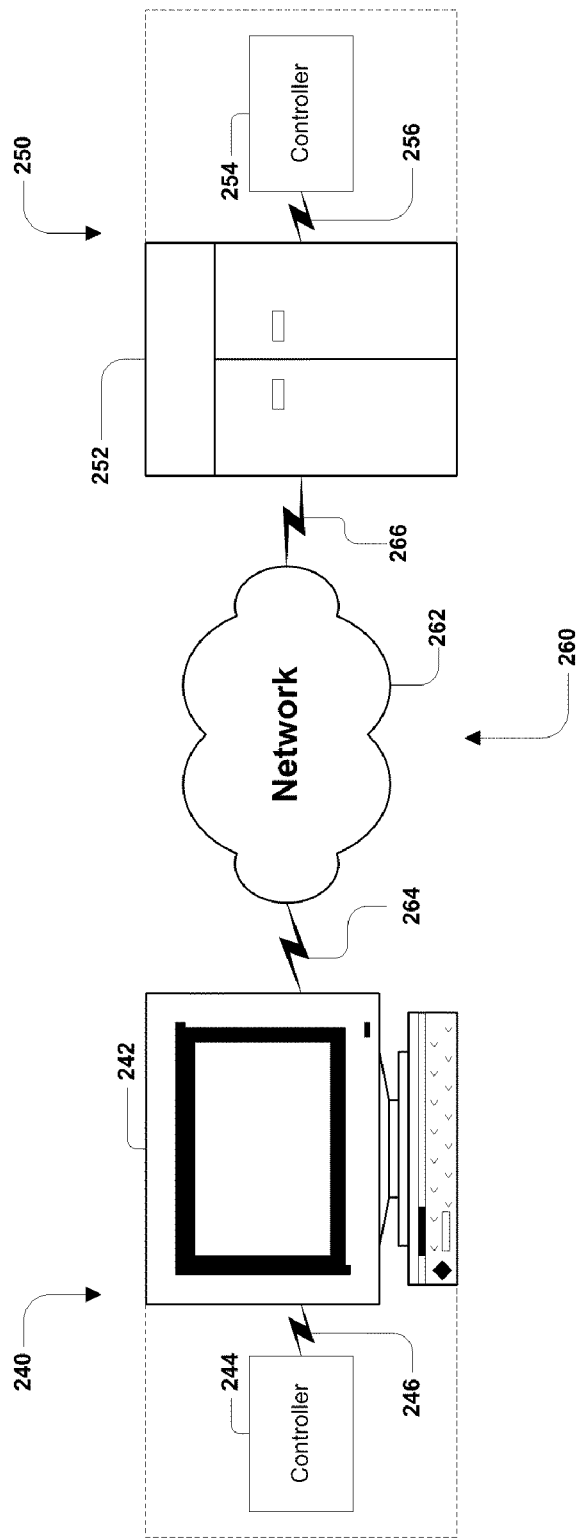

300

| | |
|---|---|
| Receive a title, a notification message, and a description of an adverse event that has occurred in a medical study | 310 |
| ↓ | |
| Determine whether the adverse event is a relatively insignificant adverse event or a relatively serious adverse event | 320 |
| ↓ | |
| Identify participants of the medical study to whom information about the adverse event will be disseminated | 330 |
| ↓ | |
| Presenting information about the adverse event to the participants of the medical study | 340 |
| ↓ | |
| Receive acknowledgement of the perception of the description of the relatively serious adverse event from the participants of the medical study | 350 |

FIG. 3

| Identifier of Adverse Event | Medical Study Identifier Associated with Adverse Event | Medical Study Type | Notification Message | Detailed Description | Comments |
|---|---|---|---|---|---|
| 1 | Leukemia Study 5 | Cancer | Death of Patient X | Patient X died of a heart attack | Stop all Treatments |
| 5 | 1256 | AIDS | SAE reported in HIV study 301 | 40 year-old white male ... | 10 |

| Identifier of Adverse Event | Participants associated with Medical Study | Acknowledged | Follow-Up Date |
|---|---|---|---|
| 1 | 50 | Yes | |
| 1 | 51 | No | 3/1/2008 |
| 1 | 52 | No | 3/2/2008 |
| 1 | 53 | Yes | |
| 5 | 60 | No | 4/5/2008 |
| 5 | 61 | Yes | |

| Identifier of Adverse Event | Type of Adverse Event | Text Color | Flashing Text | Text Size | Text Scrolling |
|---|---|---|---|---|---|
| 1 | Serious | Red | Yes | 16 | Yes |
| 5 | Insignificant | Black | No | 10 | Yes |

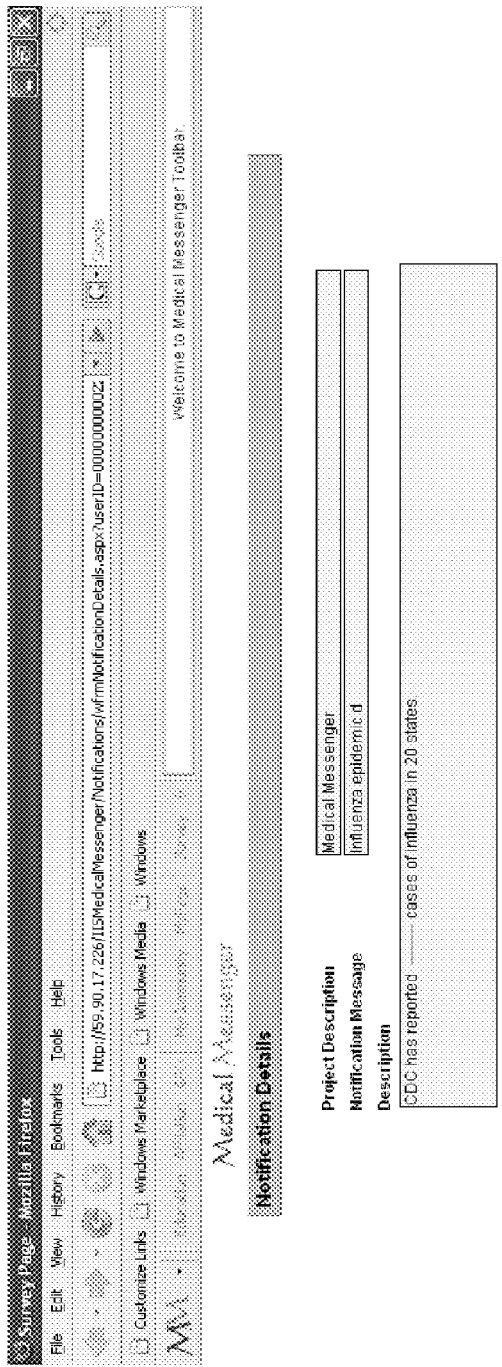
FIG. 10

| User Identifier | Survey Identifier | Survey Name | Points associated with Survey | Date Survey Completed | Date Points Allocated to User Account | Date Points Expire |
|---|---|---|---|---|---|---|
| 1 | 110 | Type of Practice | 10 | 1/18/2008 | 1/18/2008 | 1/18/2010 |
| 1 | 120 | Educational Background | 5 | 2/10/2008 | 2/11/2008 | 2/11/2009 |

PRESENTING NOTIFICATIONS RELATED TO A MEDICAL STUDY ON A TOOLBAR

CROSS-REFERENCE TO RELATED APPLICATIONS

This present application is a continuation of U.S. patent application Ser. No. 12/397,165, filed Mar. 3, 2009, which claims the benefit of U.S. Provisional Patent Application Ser. No. 61/033,391, filed on Mar. 3, 2008, the entire contents all of which are hereby incorporated by reference.

TECHNICAL FIELD

This disclosure relates to disseminating information related to adverse events occurring in a medical study to participants of the medical study, and to administering medical surveys.

BACKGROUND

Adverse events occur in medical studies that negatively affect participants of the medical studies. Disseminating information related to the adverse events to other participants of the medical study has long been a challenge for the participants of the medical study, as has encouraging and administering responses to medical surveys.

SUMMARY

In one aspect, information regarding an adverse event that has occurred in a medical study is disseminated on a toolbar. An identifier of the medical study is received and participants of the medical study to whom information regarding the adverse event will be disseminated are identified based on the identifier of the medical study. A description of a relatively insignificant adverse event that has occurred in the medical study is received. Presentation of the description of the relatively insignificant adverse event is enabled to the participants of the medical study on the toolbar. A description of a relatively serious adverse event that has occurred in the medical study is received. The severity of the relatively serious adverse event is greater relative to the severity of the insignificant adverse event. Presentation of the description of the relatively serious adverse event is enabled to the participants of the medical study on the toolbar. An acknowledgement of perception of the description of the relatively serious adverse event is received from a particular participant of the medical study.

Implementations may include one or more of the following features. For example, at least one button on the toolbar can be removed and presentation of at least part of the description of the relatively serious adverse event can be enabled on the portion of the toolbar where the at least one button was removed. The relatively serious adverse event can include an adverse event that affects patients in the medical study in a life threatening manner. The toolbar can be an element of a web browser that is perceptible by a user of the web browser.

In some implementations, a database to determine one or more text properties can be accessed for purposes of formatting a presented description of the relatively insignificant adverse event. Presentation of the description of the relatively insignificant adverse event can be enabled to the participants of the medical study on the toolbar according to the determined one or more text properties. In such implementations, a database to determine one or more text properties for purposes of formatting a presented description of the relatively serious adverse event can also be accessed. The one or more text properties for presenting the description of the relatively serious adverse event can include at least one of text color, text size, an indication that the text will be flashing, and an indication that the text will be scrolling. Presentation of the description of the relatively serious adverse event can be enabled to the participants of the medical study on the toolbar according to the determined one or more text properties. The one or more text properties for presenting the description of the relatively insignificant adverse event can be different than the one or more text properties for presenting the description of the relatively serious adverse event.

In some implementations, a notification message regarding the relatively serious adverse event to be presented to the participants of the medical study and a detailed description of the relatively serious adverse event to be presented to the participants of the medical study can be received. Presentation of the notification message regarding the relatively serious adverse event can be enabled to the participants of the medical study on the toolbar. Presentation of the detailed description of the relatively serious adverse event can also be enabled to the participants of the medical study on the toolbar.

In some implementations, an indication that the relatively serious adverse event is serious, a notification message regarding the relatively serious adverse event to be presented to the participants of the medical study, and a detailed description of the relatively serious adverse event to be presented to the participants of the medical study can be received. The particular participant of the medical study can be required to acknowledge their perception of the description of the relatively serious adverse event in response to receiving the indication that the relatively serious adverse event is serious.

An indication of perception of the description of the relatively serious adverse event and a comment associated with the relatively serious adverse event can be received from a particular participant of the medical study. An indication that a particular participant of the medical study will later acknowledge perception of the description of the relatively serious adverse event can be received from the particular participant of the medical study.

In some implementations, a date of receiving the indication that the particular participant of the medical study will later acknowledge perception of the description of the relatively serious adverse event can be identified. A predetermined time period for following up with the particular participant of the medical study that will later acknowledge perception of the description of the relatively serious adverse event can be accessed from a database. Presentation of a notification requesting acknowledgement of perception of the description of the relatively serious adverse event after a predetermined time period can be enabled to the particular participant of the medical study that will later acknowledge perception of the description of the relatively serious adverse event.

In some implementations, the participants of the medical study that have not acknowledged perception of the description of the relatively serious adverse event can be determined, and presentation of a notification requesting acknowledgement of perception of the description of the relatively serious adverse event can be enabled to the participants of the medical study have not acknowledged perception of the description of the relatively serious adverse event.

In some implementations, a database storing identifiers of participants of one or more medical studies and identifiers of the one or more medical studies can be accessed. The identifier of a medical study can be compared with the stored identifiers of the one or more medical studies, and an identifier of the medical study that is equal to one of the stored identifiers of the one or more medical studies can be determined. Identifiers of the participants of the medical study can be retrieved based on the determination that the identifier of the medical study is equal to one of the stored identifiers of the one or more medical studies.

In some implementations, an indication that a particular participant has selected the description of the relatively serious adverse event positioned on the toolbar can be received, and presentation of a web page including a selectable button enabling acknowledgement of perception of the description of the relatively serious adverse event can be enabled to the particular participant and in response to receiving the indication that the particular participant has selected the description of the relatively serious adverse event.

In another aspect information regarding an adverse event that has occurred in a medical study is disseminated on a toolbar. An identifier of the medical study is received, and participants of the medical study to whom information regarding the adverse event will be disseminated are identified based on the identifier of the medical study. A description of an adverse event that has occurred in the medical study is received, and presentation of the description of the adverse event is enabled to an authority. An indication of whether the adverse event is a relatively insignificant adverse event or a relatively serious adverse event is received. The severity of the relatively serious adverse event is greater relative to the severity of the insignificant adverse event. The participants of the medical study are required to acknowledge perception of the description of the relatively serious adverse event in response to receiving an indication that the adverse event is a relatively serious adverse event. Presentation of the description of the adverse event is enabled to the participants of the medical study on the toolbar. An acknowledgement of perception of the description of the relatively serious adverse event is received from a particular participant of the medical study.

The various aspects, implementations, and features may be implemented using, for example, one or more of a method, an apparatus, a system, an apparatus, system, tool, or processing device for performing a method, a program or other set of instructions, an apparatus that includes a program or a set of instructions, and a computer program embodied in a tangible computer readable medium. The tangible computer readable medium may include, for example, instructions, software, images, and other data.

For example, a tangible computer-readable medium can have embodied thereon a user interface configured to disseminate information regarding an adverse event that has occurred in a medical study. The user interface includes a first interface element structured and arranged to display at least one button associated with a first webpage. The at least one button is selectable by a user perceiving the user interface to inspire display of the first webpage. The user interface also includes a second interface element structured and arranged to display a description of an adverse event that has occurred in a medical study. The second interface element is selectable by the user perceiving the user interface to inspire display of a second webpage including a detailed description of the adverse event that has occurred in the medical study. The second webpage is different than the first webpage. The second interface element has a first size to display a description of a relatively serious adverse event and a second size to display a description of a relatively insignificant adverse event. The first size is greater than the second size.

Implementations may include one or more of the following features. For example, the relatively serious adverse event is an adverse event that has a severity greater than a predetermined threshold. The second interface element can be structured and arranged to display a description of an adverse event according to one or more text properties. The text properties for displaying a description of the relatively serious adverse event can be different than the text properties for displaying a description of the relatively insignificant adverse event.

Details of one or more implementations are set forth in the accompanying drawings and the description below.

DESCRIPTION OF DRAWINGS

FIG. 1b is an illustration of a user interface displayed on a graphical user interface display device that enables a user of the toolbar to complete a survey.

FIG. 2b is a block diagram of an example of a communications system capable of delivering and exchanging data.

FIG. 3 is a flowchart of an example of a process for disseminating information regarding an adverse event that has occurred in a medical study on a toolbar.

FIG. 5 is an illustration of an example of an adverse event detail data structure.

FIG. 6 is an illustration of an example of an acknowledgement data structure.

FIG. 8 is an illustration of an example of an adverse event presentation data structure.

FIGS. 9-11 are illustrations of user interfaces displayed on a graphical user interface display device that enable presentation of additional information associated with adverse events.

FIG. 13 is an illustration of an example of a survey data structure.

DETAILED DESCRIPTION

Figure 1A:
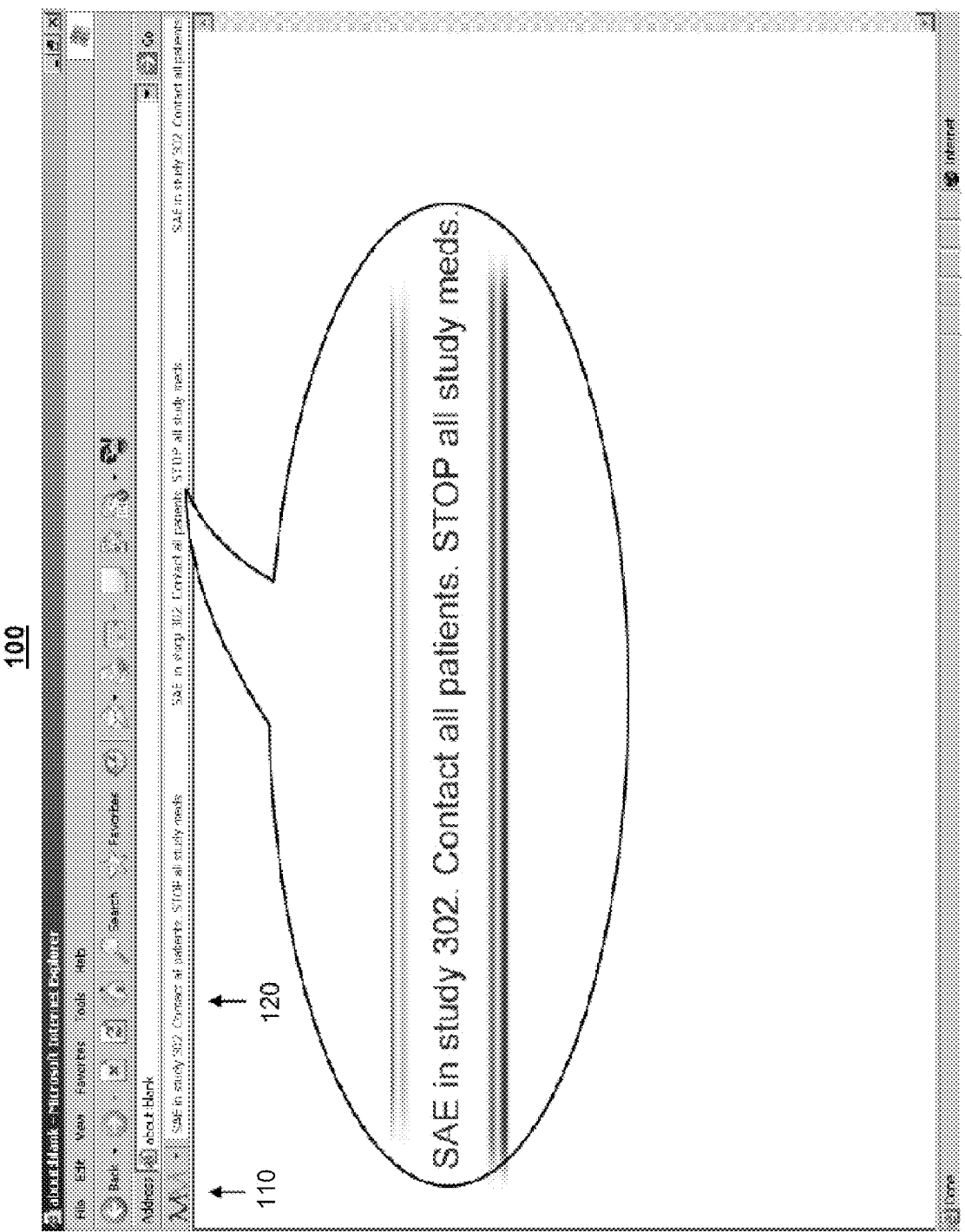
FIG. 1a is an illustration of a user interface displayed on a graphical user interface display device that enables a participant of a medical study to be notified of and perceive serious adverse events.
Figure 9:
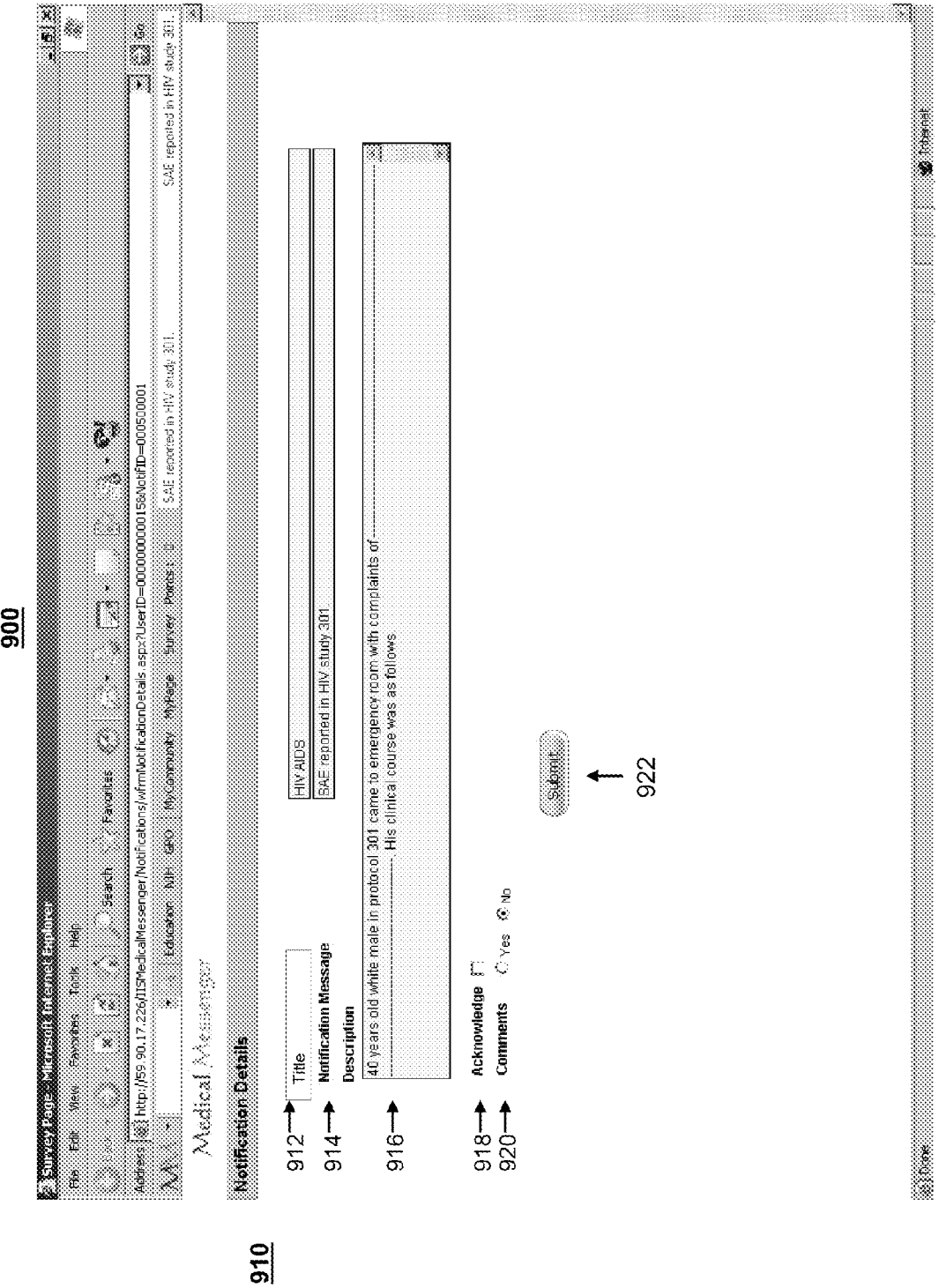
Figure 11:
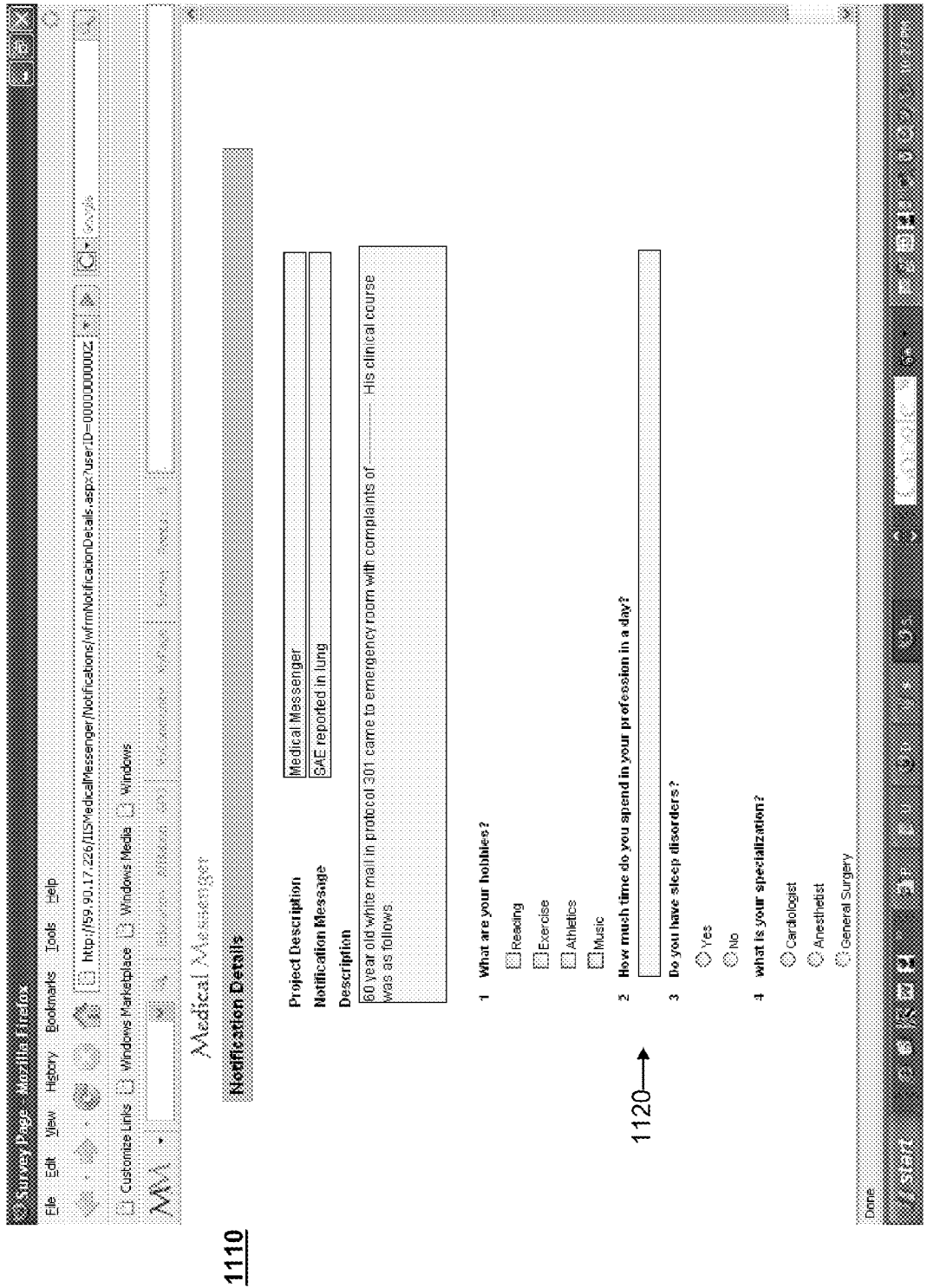

FIG. 1a is an example of a user interface 100 that enables a participant of a medical study to be notified of and perceive serious adverse events. The user interface 100 includes a toolbar 110 having block 120 to present notifications of the serious adverse advents. The notifications of the serious adverse events may be repetitively scrolled across block 120 in a different type, color, and/or size font from notifications of insignificant adverse events. Serious adverse events include adverse events having severity greater than insignificant adverse events, having severity greater than a predetermined threshold, requiring hospitalization, and/or being life-threatening. Insignificant adverse events include adverse events that affect patients in an unexpected manner. In addition, the notifications are selectable, by clicking anywhere in block 120, such that the participant viewing a notification will receive additional information about the serious adverse event related to the notification, as illustrated in FIGS. 9 to 11.

FIG. 1*b* is an example of a survey user interface 150 that enables a user of the toolbar to complete a survey. The survey user interface 150 includes webpage 160. Webpage 160 includes survey questions 170, a button 180 selectable by the user to submit responses to the survey questions 170, and a button 190 selectable by the user of the toolbar to exit the survey webpage 160. The responses to the survey questions may be completed by user of the toolbar interacting with radio buttons, selectable boxes, or data entry blocks. Once the user submits responses to the survey questions 170 by selecting button 180, the survey information, including the points associated with the survey, may be added to a survey data structure, as illustrated in FIG. 13.

Figure 2A:
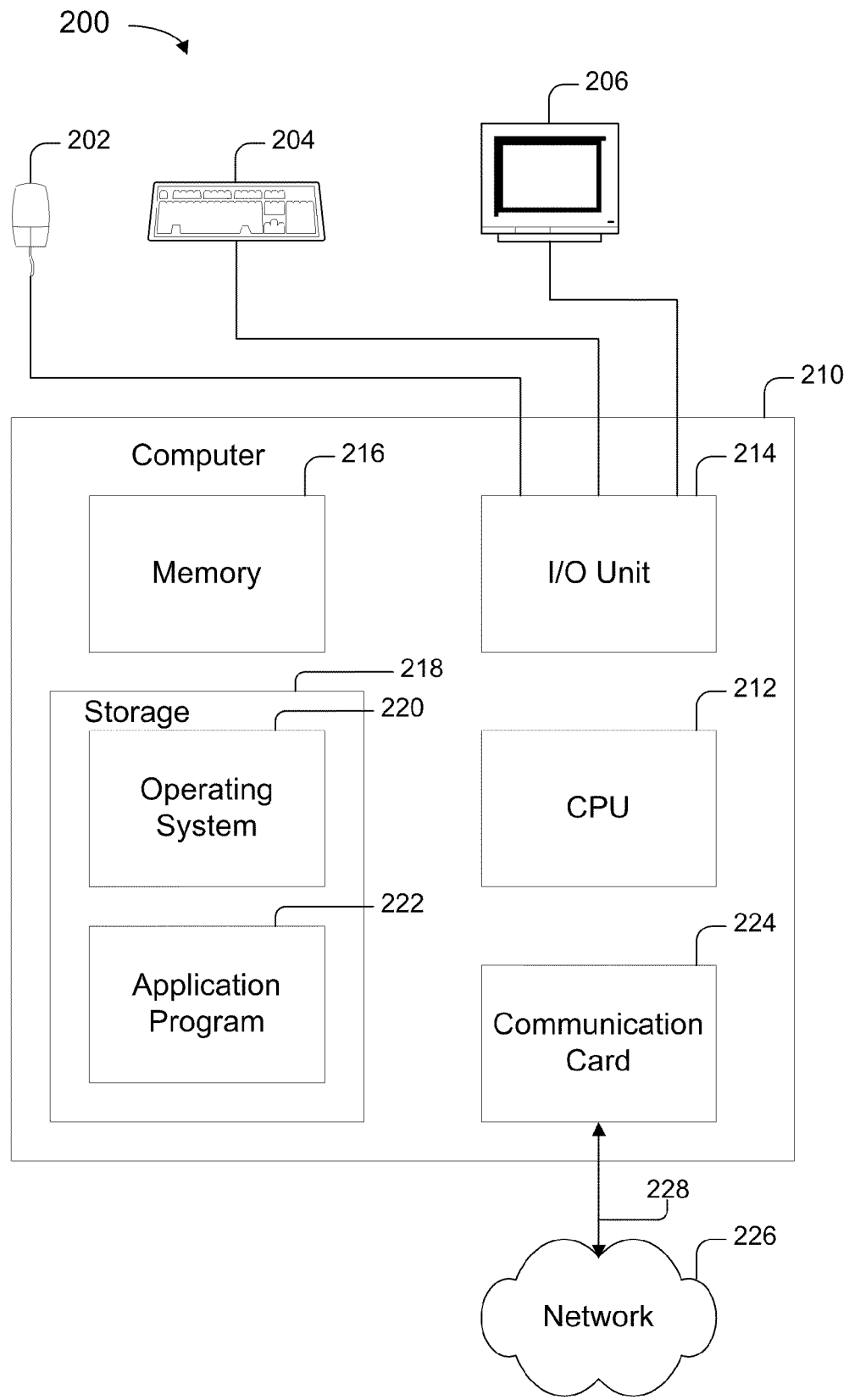
FIG. 2a is a block diagram of an example of a system for sending and/or receiving adverse event information, sending and/or receiving medical survey information, and displaying a toolbar.

Referring to FIG. 2*a*, exemplary components of a system 200 that may be used to send and/or receive adverse event information, send and/or receive medical survey information, and display a toolbar, is shown. The hardware setup may include various input/output (I/O) devices (e.g., mouse 202, keyboard 204, and display 206) and general purpose computer 210 having central processor unit (CPU) 212, I/O unit 214, memory 216, and storage 218 that stores data and various programs such as operating system 220 and one or more application programs 222. Computer system 210 also includes a communications card or device 224 (e.g., a modem or a network adapter) for exchanging data with a network 226 via a communications link 228 (e.g., a telephone line, a wireless network link, a cable network). Other examples of system 200 include a workstation, a server, a device, a component, other equipment of some combination thereof capable of responding to and executing instructions in a defined manner. The CPU 212 can be, by way of example, a general or special purpose microprocessor. Generally, the CPU 212 will receive instructions and data from a memory, such as the memory 216.

Referring to FIG. 2*b* a communications system 230 is capable of delivering and exchanging data between a client system 240 and a host system 250 through a communications link 260. The client system 240 typically includes one or more client devices 242 and/or client controllers 244, and the host system 250 typically includes one or more host devices 252 and/or host controllers 254. For example, the client system 240 or the host system 250 may include one or more general-purpose computers (e.g., personal computers), one or more special-purpose computers (e.g., devices specifically programmed to communicate with each other and/or the client system 240 or the host system 250), or a combination of one or more general-purpose computers and one or more special-purpose computers. The client system 240 and the host system 250 may be arranged to operate within or in concert with one or more other systems, such as, for example, one or more LANs ("Local Area Networks") and/or one or more WANs ("Wide Area Networks").

The client device 242 (or the host device 252) may have the hardware and architecture of the system 200 of FIG. 2*a*. The client device 242 (or the host device 252) is generally capable of executing instructions under the command of a client controller 244 (or a host controller 254). The client device 242 (or the host device 252) is connected to the client controller 244 (or the host controller 254) by a wired or wireless data pathway 246 or 256 capable of delivering data.

An example of client controller 244 or a host controller 254 is a software application loaded on the client device 242 or the host device 252 for commanding and directing communications enabled by the client device 242 or the host device 252. Other examples include a program, a piece of code, an instruction, a device, a computer, a computer system, or a combination thereof, for independently or collectively instructing the client device 242 or the host device 252 to interact and operate as described. The client controller 244 and the host controller 254 may be embodied permanently or temporarily in any type of machine, component, physical equipment, or storage medium capable of providing instructions to the client device 242 or the host device 252.

The communications link 260 typically includes a delivery network 262 making a direct or indirect communication between the client system 240 and the host system 250, irrespective of physical separation. Examples of a delivery network 262 include the Internet, the World Wide Web, WANs, LANs, analog or digital wired and wireless telephone networks (e.g., PSTN, ISDN, and xDSL), radio, television, cable, satellite, and/or any other delivery mechanism for carrying data. The communications link 260 may include communication pathways 264, 266 that enable communications through the one or more delivery networks 262 described above. Each of the communication pathways 264, 266 may include, for example, a wired, wireless, cable or satellite communication pathway.

FIG. 3 illustrates a flow diagram of a process 300 to disseminate information regarding an adverse event that has occurred in a medical study on a toolbar. A system associated with an administrator of a medical study, such as host device 252, receives information about an adverse event that has occurred in the medical study (step 310). The information about the adverse event may be entered by the administrator using host device 252 or may be entered by a participant of the medical study using client device 242. Information entered by the participant, may be forwarded to the administrator system.

Figure 4:
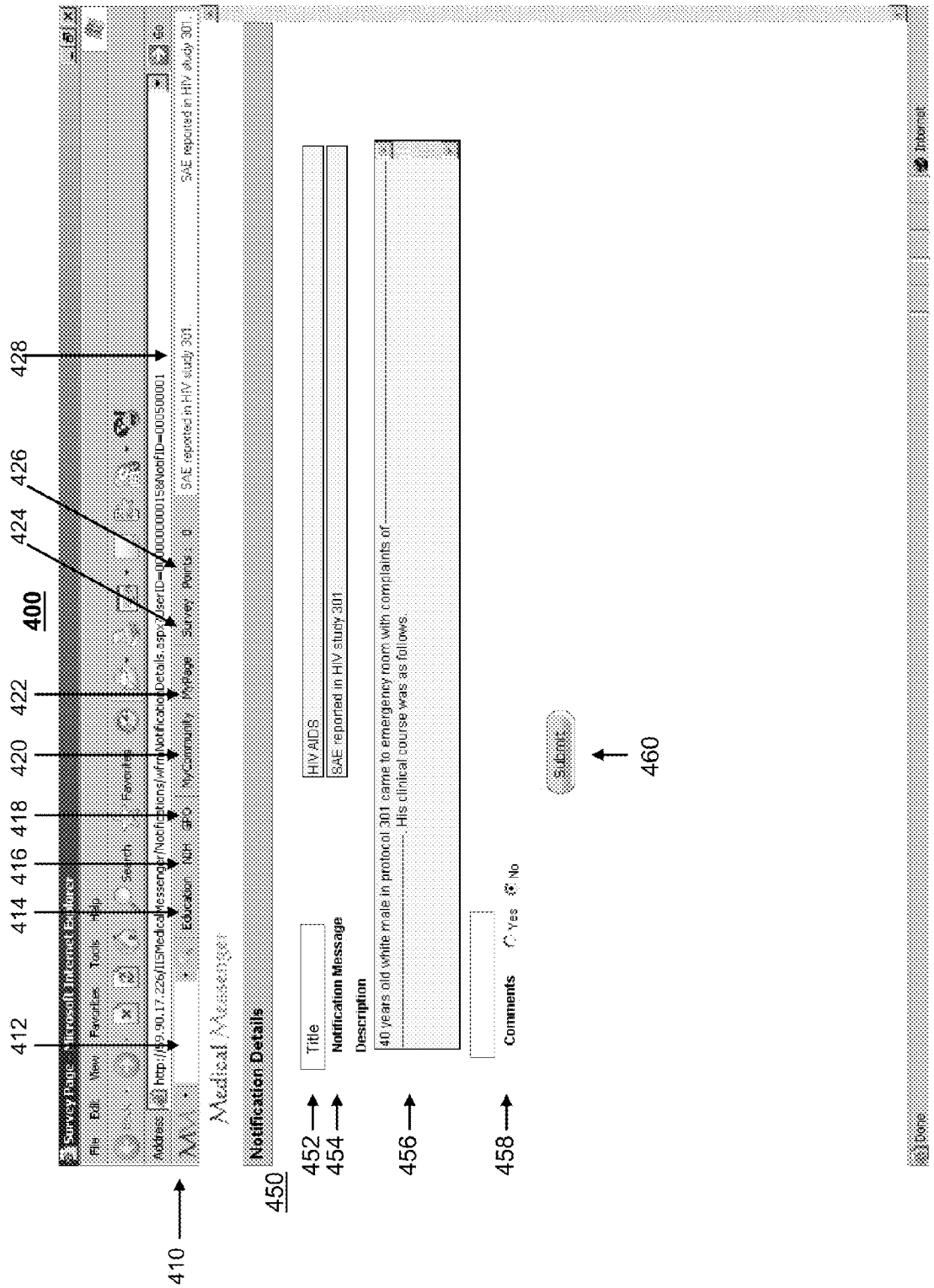
FIG. 4 is an illustration of a user interface displayed on a graphical user interface display device that enables entry of information associated with an adverse event.

The participant of the medical study may enter the adverse event information in a user interface, such as the user interface of FIG. 4, or by use of telephone, facsimile, and/or electronic mail. As illustrated in FIG. 4, data entry web page 450 enables entry of a title 452, a notification message 454, and a detailed description 456 of the adverse event. Comments 458 associated with the adverse event may also be entered. FIG. 4 also illustrates toolbar 410, which is described in greater detail below.

This information entered in the data entry web page 450 is stored in adverse event detail data structure 500, as illustrated in FIG. 5. Field 510 stores adverse event identifiers. The identifiers may include numerical identifiers, such as "1" or "5," created by the client device 242 or the host device 252. Alternatively, the adverse event identifiers may be submitted by a participant submitting the information related to the adverse event. If the participant submits the adverse event identifier, a search may be performed to determine whether the submitted identifier has already been assigned to a previously submitted adverse event and, if the adverse event identifier has already been assigned to a previously submitted adverse event, the participant will be required to submit a different adverse event identifier. In addition, if the adverse event identifier has already been assigned to a previously submitted adverse event, available adverse event identifiers may be suggested to the participant submitting the information related to the adverse event.

Field 520 stores medical study identifiers, such as the title 452 of the medical study entered by the participant of the medical study. The medical study identifier field 520 may alternatively store a numerical identifier of the medical study, such as "1255." Field 530 stores medical study types that identify the type of medical study associated with an adverse event. For example, the medical study associated with an adverse event may be a cancer study or an AIDS study. The participant of the medical study may enter the medical study type in the data entry web page 450 or the host device 252 may determine the medical study type based on additional information stored about the medical study in the host device 252.

Field 540 stores notification messages 454 entered in web page 450. The notification messages may also be selected by the participant of the medical study from a group of predetermined notification messages associated with various adverse events. For example, a medical study may require a particular notification message to be associated with a particular type of adverse event. Because the notification messages are presented to participants of the medical study on the toolbar, the notification messages may be limited to a predetermined number of characters. In addition, if the text scrolling indication 860 indicates that the notification message will be presented on the toolbar as scrolling text, the maximum notification message length may be greater than if the text scrolling indication 860 indicates that the information associated with the adverse event will not be presented on the toolbar as scrolling text.

Field 550 stores descriptions 456 entered in web page 450. The descriptions may be presented to participants of the medical study on the toolbar or in a web page or e-mail. The length of the descriptions 456 may also be limited to a predetermined number of characters, but the limit for the descriptions will be greater that the limit for the notification messages.

Field 560 stores comments 458 entered in web page 450. Like the descriptions, the comments may also be presented to participants of the medical study on the toolbar or in the web page or e-mail presenting the descriptions of the adverse events.

In addition, the adverse event detail data structure 500 may be configured to include a field (not shown) to store the times and dates that information related to the adverse events are submitted and another field (not shown) to store identifiers of the participants of the medical study who submit the information related to the adverse events. An identifier of a participant may be the participant's name or a surrogate identifier, such as a numerical identifier identifying the participant. Another field (not shown) may be included to store the times and the dates that the adverse events occurred and another field (not shown) to store the addresses (including some or all of the street, city, zip code, county, and country) indicating where adverse events occurred. Finally, the adverse event detail data structure 500 may include a field (not shown) to store whether the patients suffering the adverse events were under medical supervision when the adverse events occurred.

Referring back to FIG. 3, next, the system associated with the administrator of the medical study determines whether the adverse event is an insignificant adverse event or a serious adverse event (step 320). The indication of whether an adverse event is insignificant or serious is stored in the adverse event presentation data structure 800, as illustrated in FIG. 8. In one example, the participant of the medical study who enters the information associated with the adverse event provides an indication of whether the adverse event is insignificant or serious. In another example, the administrator of the medical study determines whether the adverse event is insignificant or serious based on the description 456 of the adverse event. For example, any adverse event that requires hospitalization or is life-threatening may be determined to be a relatively serious adverse event.

Alternatively, the system associated with the administrator of the medical study may determine the level of severity of the adverse event. For example, the severity of adverse events may be categorized into five levels. In this example, adverse events having a severity level equal to or greater than the third most severe level are determined to be relatively serious, and the other adverse events are determined to be relatively insignificant. In another example, the five levels may include "actionable," "cautionary," "general," "mandatory," and "red alert." In this example, only those adverse events categorized as "mandatory" or "red alert" may be determined to be relatively serious and those categorized as "actionable," "cautionary," or "general" may be determined to be relatively insignificant. As such, serious adverse events are determined have a severity greater than an insignificant adverse event.

Next, participants of the medical study to whom information about the adverse event will be disseminated are identified (step 330). To identify these participants of the medical study, the identifier of an adverse event of interest is retrieved from field 510 of the adverse event detail data structure 500. The identifier of the adverse event is used to search field 610 of an acknowledgement data structure 600 illustrated in FIG. 6. Field 610 of the acknowledgement data structure 600 may store all of the same adverse event identifiers as stored in field 510 of the adverse event detail data structure 500. Alternatively, only some of the adverse events stored in adverse event detail data structure 500 may be stored in the acknowledgement data structure 600. For example, if a medical study only requires serious adverse events to be acknowledged, without requiring the insignificant adverse events to be acknowledged, the acknowledgement data structure 600 may be configured to store only information related to the serious adverse events. In this example, the identifier 510 of adverse events stored in the adverse event detail data structure 500 which are determined to be insignificant are not copied to the acknowledgement data structure 600. Thus, less memory is required to store the acknowledgement data structure 600 than if the acknowledgement data structure 600 stored information related to all of the adverse events.

Once the identifier of the adverse event is found in field 610, the identifiers of the participants associated with the medical study from which the adverse event originated are retrieved from field 620. For each adverse event identifier, field 620 stores identifiers of participants associated with the medical study from which the adverse event originated. For example, as illustrated in FIG. 6, participants 50, 51, 52, and 53 are associated with the medical study from which adverse event 1 originated, whereas participants 60 and 61 are associated with the medical study from which adverse event 2 originated. Field 620 may store information for all of the participants associated with the medical study or a subset of the participants associated with the medical study. For example, only group leaders and/or participants required to acknowledge the adverse event may be included in field 620. In another example, participants may be removed from the acknowledgement data structure 600 once they acknowledge the adverse event to reduce the memory required to store the acknowledgement data structure 600.

Next, the information about the adverse event is presented to the identified participants of the medical study (step 340). If the adverse event is a serious adverse event, the user interface 100 of FIG. 1a including the toolbar 110 having block 120 is presented to the identified participants of the medical study. If the adverse event is an insignificant adverse event, a user interface 700 of FIG. 7 including toolbar 710 having block 720 is presented to the identified participants of the medical study.

Figure 7:
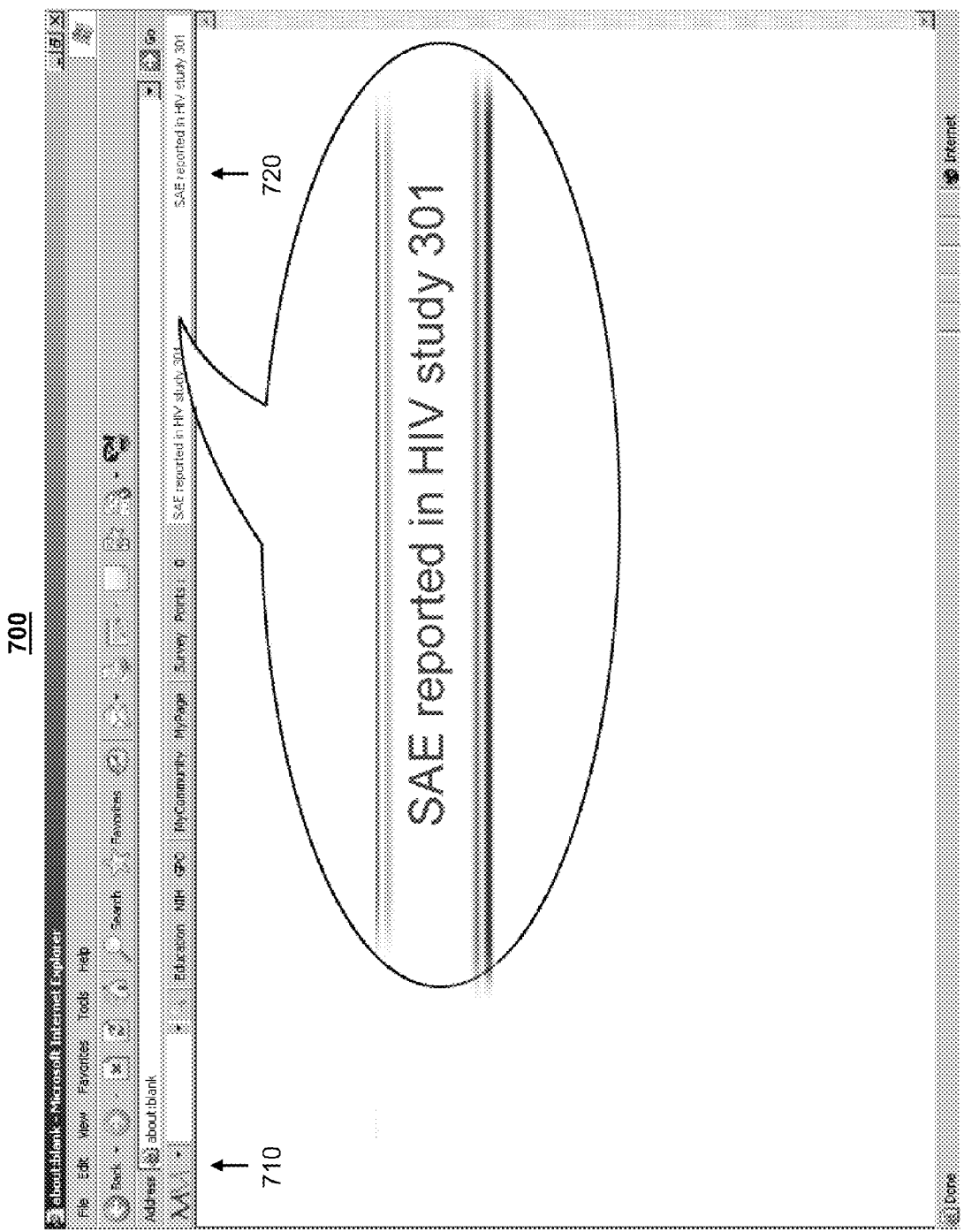
FIG. 7 is an illustration of a user interface displayed on a graphical user interface display device that enables a participant of a medical study to be notified of and perceive insignificant adverse events.

In FIG. 7, the configuration of the toolbar 710 remains unchanged, whereas in FIG. 1a, search entry block 412, buttons 414, 416, 418, 420, 422, and 424, and indication 426 (of the toolbar 410 of FIG. 4) are removed from the toolbar 110 so that block 120 spans almost the entire toolbar 110. The user of toolbar 110 may choose which buttons are removed to expand block 120, such that the size of block 120 for two different users of toolbar 110 will differ. Expanding block 120 is advantageous in that it allows a user of the toolbar 110 to quickly determine that an adverse event is serious and requires immediate attention.

The configuration of the toolbar may be determined based on an indication of whether the adverse event is serious or insignificant, such as the adverse event type indicator 820 of the adverse event presentation data structure 800, illustrated in FIG. 8. If the adverse event type indicator 820 indicates that an adverse event is a serious adverse event, the toolbar 110 is configured with an expanded block 120 and the visual display of the blocks selected by the user of the toolbar 110 to be removed are no longer displayed within toolbar 110. If the adverse event type indicator 820 indicates that an adverse event is insignificant, the toolbar 710 remains unchanged.

To present the information associated with the adverse event, the notification message of the adverse event is retrieved from field 540 of the adverse event detail data structure 500. In addition, the detailed description of the adverse event may be retrieved from field 550 and the title may be retrieved from field 520 to be displayed in block 120 or 720. The system will also retrieve presentation characteristics of the adverse event information from an adverse event presentation data structure 800. First, the adverse event identifiers 810 of the adverse event presentation data structure 800 are searched to identify the adverse event to be presented. Next, the type of adverse event, insignificant or serious, is retrieved from field 520 to configure the toolbar used to present the information associated with the adverse event.

The presentation characteristics of the text used to present the information are then retrieved from fields 830, 840, 850, and 860 of the adverse event presentation data structure 800. Field 830 stores text colors, field 840 stores flashing text indications, field 850 stores text sizes, and field 860 stores scrolling text indications. These characteristics may be submitted by the participant who submits the adverse event or by an administrator of the medical study. Alternatively, these characteristics may be default characteristics based on the type of the adverse event that may be changed for a specific adverse event. In this example, the presentation characteristics of two serious adverse events or two insignificant adverse events may be different.

As another alternative, the adverse event presentation data structure 800 may not include fields 830, 840, 850, and 860, and the presentation characteristics of text colors, flashing text indications, text sizes, and scrolling text indications are extracted from a lookup table. In this example, adverse events of a specific type share the same presentation characteristics, and the lookup table would be used to determine the presentation characteristics based on the type or severity level of the adverse event. The presentation characteristics of insignificant adverse events and serious adverse events may be different. For example, a serious adverse event may be presented in a brighter text color and a larger text size. In addition, the description of only serious adverse events may flash and scroll across the toolbar to attract the attention of the participant using the toolbar.

After the system has retrieved the notification message from field 540 and the presentation characteristics from the adverse event presentation data structure 800, the notification message for the adverse event will be presented according to the presentation characteristics in block 120 or 720, depending on whether the adverse event is insignificant or serious.

Finally, the system associated with the administrator of the medical study will receive acknowledgement of the perception of the description of a relatively serious adverse event from the participants of the medical study (step 350). To acknowledge perception of the description of a relatively serious adverse event, a participant may select a button (not shown) on the toolbar 110 or 710. Alternatively, the participant may request additional information about the adverse event before acknowledging perception of the description of a relatively serious adverse event. To receive additional information about the adverse event, the participant selects block 120 or 720 by clicking anywhere in block 120 or 720.

In response to the participant's selection of block 120 or 720, the adverse event identifier associated with the adverse event of interest is located in field 510 of the adverse event detail data structure 500. The medical study identifier (title) of the medical study is retrieved from field 520, the notification message is retrieved from field 540, and the detailed description is retrieved from field 550 for the adverse event of interest. The medical study identifier, notification message, and detailed description are used to generate a user interface, such as the user interface 900 of FIG. 9, presented to the participant of the medical study requesting additional information about the adverse event.

User interface 900 includes a web page 910 including additional information about the adverse event. Web page 910 includes an identifier (title) of the medical study 912 from which the adverse event originated, the notification message 914 associated with the adverse event, a detailed description 916 associated with the adverse event, a box 918 to confirm acknowledgment of the adverse event, radio buttons 920 for selecting to provide comments, and button 922 for submitting the acknowledgement and comments.

By selecting box 918, a participant of the medical study may acknowledge that he or she has viewed the description of the adverse event. In one example, once the participant submits acknowledgement, the value in field 630 of the adverse event detail data structure 500 for the participant will change from "No" to "Yes." In another example, the participant will be removed from the acknowledgement data structure 600 after submitting acknowledgement. If the toolbar 110 or 710 includes a button (not shown) selectable by the user to acknowledge the adverse event, field 630 of the adverse event detail data structure 500 will be updated in the same way.

If the participant selects the "Yes" radio button 922 for selecting to provide comments, another data entry block (not shown) may be provided on the web page 910 for entering the comments. Alternatively, radio buttons 920 may be replaced with a data entry block such that comments, if any, may be provided without having to choose an option to provide comments.

FIG. 10 illustrates another example of a user interface 1000 to present additional information associated with the adverse event. Like user interface 900 which includes web page 910, user interface 1000 includes web page 1010. And, like web page 910, web page 1010 includes an identifier (title) of the medical study from which the adverse event originated, a notification message associated with the adverse event, and a detailed description associated with the adverse event retrieved from adverse event detail data structure 500. Web page 1010 additionally includes button 1020 to submit acknowledgement of the adverse event and button 1030 to submit that the participant will come back to web page 1010 to acknowledge the adverse event at a later time.

Once the participant selects button 1020, the value in field 630 of the adverse event detail data structure 500 for the participant will change to "Yes" or the participant will be removed from the acknowledgement data structure 600. If the participant selects button 1030, a follow-up date will be determined and stored in field 640 of the adverse event detail data structure 500.

The follow-up dates stored in field 640 are determined as a predetermined time from the date that the adverse event occurred, the date that the adverse event was submitted, or the date that the adverse event was first presented to the participant. In one example, the predetermined time may be received from the participant or an organizer of the medical study. In another example, the follow-up date may be determined based on the requirements of the medical study.

Alternatively, the participant may provide a specific follow-up date to be stored in field 640. In this example, the specific follow-up date stored in field 640 is retrieved and acknowledgement of the adverse event is requested on that date.

The acknowledgement data structure 600 may also include a field (not shown) to store the date that the adverse event was first presented to the participant and a field to store the date that the adverse event was last presented to the participant. For example, a participant may be reminded to acknowledge the adverse event using the toolbar during the first week after adverse event occurred. If an acknowledgement is not received in the first week, an e-mail and/or facsimile message may be forwarded to the participant. In another example, a participant may be reminded to acknowledge the adverse event using the toolbar a predetermined number of times, such as three times. If acknowledgement is not received after the third toolbar reminder, an e-mail and/or facsimile message may be forwarded to the participant. The date that the adverse event was last presented to the participant may be used to determine when the next reminder should occur.

Furthermore, the predetermined time used to determine the follow-up dates may be varied based on the elapsed time from which the adverse event occurred, the adverse event was submitted, or the adverse event was first presented to the participant. For example, in the first month from the occurrence of the adverse event, a participant who has not acknowledged the adverse event may be reminded once a week. However, after the first month, the participant may be reminded every day. Similarly, the first three reminders may be provided once a week, but after the third reminder, the participant may be reminded every day.

In another example, a medical study may require that all participants acknowledge an adverse event no later than one week or one month from the date that the adverse event occurred. In such an example, the participants who have not acknowledged the adverse event may be reminded to do at an increased frequency as the deadline for acknowledgement is approached.

On the follow-up date, the participant will be reminded to acknowledge the adverse event. The reminder may be displayed on the toolbar, included in an electronic mail (e-mail) message, included in a facsimile message, included in a letter sent to the participant's preferred address, and/or included as part of an automated voice message.

In one example, web page 1010 may be presented to a participant of the medical study if the medical study requires acknowledgment of the adverse event, such as when the adverse event has been categorized as serious, whereas web page 910 may be presented to the participant if the medical study does not require acknowledgement of the adverse event, such as when the adverse event has been categorized as insignificant. In another example, the participant of the medical study or an administrator of the medical study may selectively choose web page 910 or web page 1010 for all adverse events.

FIG. 11 illustrates another example of a user interface 1100 to present additional information associated with the submitted adverse events. Like web page 910, web page 1110 includes an identifier of the medical study from which the adverse event originated, a notification message associated with the adverse event, and a detailed description associated with the adverse event retrieved from adverse event detail data structure 500.

Web page 1110 additionally includes survey questions 1120 presented to the participant to collect additional information about the participant. The survey questions may include demographic questions about the participant, questions about the participant's interests, and/or questions about the participant's occupation. Alternatively, the survey questions may be surveys related to survey identifiers 1320 associated with the user identifier 1310 of the participant accessed from the survey data structure 1300 of FIG. 13, described in greater detail below. Once the participant completes the survey questions, the answers are submitted by selecting a button on the web page 1110. Points may be deposited into an account for the participant for each survey completed by the participant, as explained in greater detail below.

Referring back to FIG. 4, user interface 400 includes a toolbar 410. The toolbar 410 includes a search entry block 412, a button 414 selectable by a user of the toolbar to access an educational web page, a button 416 selectable by a user of the toolbar to access a web page for an organization, a button 418 selectable by a user of the toolbar to access a web page of the user's employer, a button 420 selectable by a user of the toolbar to access a community web page, a button 422 selectable by a user of the toolbar to access a personal web page, and a button 424 selectable by a user of the toolbar to access a survey that the user may complete to collect points. The toolbar 410 also includes an indication 426 of a number of points collected by the user, and a block 428 to present information, such as a notification message associated with an adverse event. The toolbar may also include a button (not shown) selectable by the user of the toolbar to acknowledge the adverse event.

The user of the toolbar enters a term in the search entry block 412 to search for that term on the Internet. The term is temporarily stored by the client device 242 and forwarded to a default search service or a user selected search service, which uses the term to search for that term on the Internet. The user selects button 414 to receive an educational web page associated with button 414. The educational web page may be a default educational web page, may be selected by the user, or may be automatically selected based on the background of the user stored in a user profile of the user. For example, if the user of the toolbar is a radiologist, the educational web page may provide continuing education for radiologists.

The user selects button 416 to receive a web page for an organization of interest to the user. For example, the user may be interested in applying for grants from the National Institutes of Health (NIH) and, thus, have an interest in keeping up with information released from NIH. The user may associate the main NIH web page or a particular web page related to NIH with button 416. Thereafter, the user selects button 416 to receive the web page related to NIH. The user selects button 418 to receive a web page for the user's employer. The web address for the user's employer may be entered by the user or determined based on the user's profile. For example, the user may be employed by "GPO" and, thus, button 418 is associated with the main GPO web page or a particular GPO web page, such as a specific department web page.

The user selects button 420 to receive a community web page, such as an online forum. The community web page may be a default community page or a community page selected by the user. For example, if the user has joined a medical community forum, he can associate button 420 with that forum. The user selects button 422 to receive a personal web page, such as a personalized portal page. The personalized web page includes information customized to the interests of the user. The interests of the user may be selected by the user or may be selected based on the user's profile. For example, the user's answers to survey questions may be used to select the user's interests to personalize the portal page without any user intervention.

The user selects button 424 to access surveys. Survey information is stored in the survey data structure 1300 of FIG. 13, which is accessed in response to user selection of button 424. The survey data structure 1300 includes a user identifier field 1310, a survey identifier field 1320, a survey name field 1330, a points associated with each survey field 1340, a survey completion date field 1350, a point allocation date field 1360, and a point expiration date field 1370.

In particular, once the user selects button 424, the user identifier 1310 of the user is determined and survey identifiers 1320 associated with the user are accessed from the survey data structure 1300. The surveys that have not been completed by the user are identified and one of the uncompleted surveys is presented to the user. In another example, the user receives a list of one or more uncompleted surveys. The user then selects one of the surveys to complete. Each survey will have a particular point value 1340 associated with it that may be presented to the user to motivate the user to complete the survey. Once the user completes a survey, the point value associated with the survey is deposited into an account associated with the user.

Figure 14:
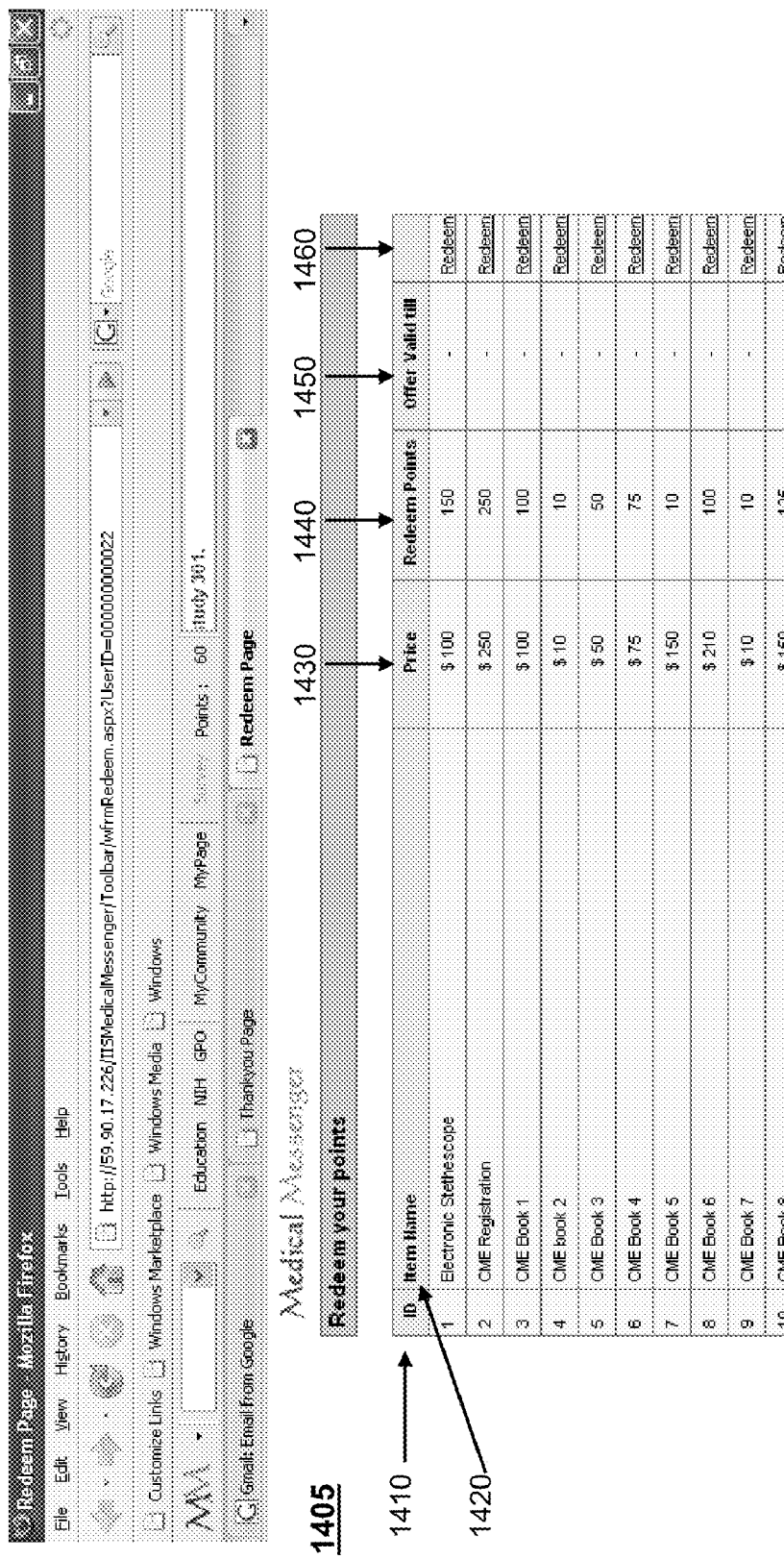
FIG. 14 is an illustration of a user interface displayed on a graphical user interface display device that enables a user to redeem points accumulated for completing surveys.

The user selects indication 426 to receive more information about the points earned by the user, such as the information stored in fields 1330-1370 of the survey data structure 1300. This information is extracted from the survey data structure 1300 and presented to the user. In another example, the user may select indication 426 to view a user interface 1400 for redeeming the points collected, as illustrated in FIG. 14.

Figure 12:
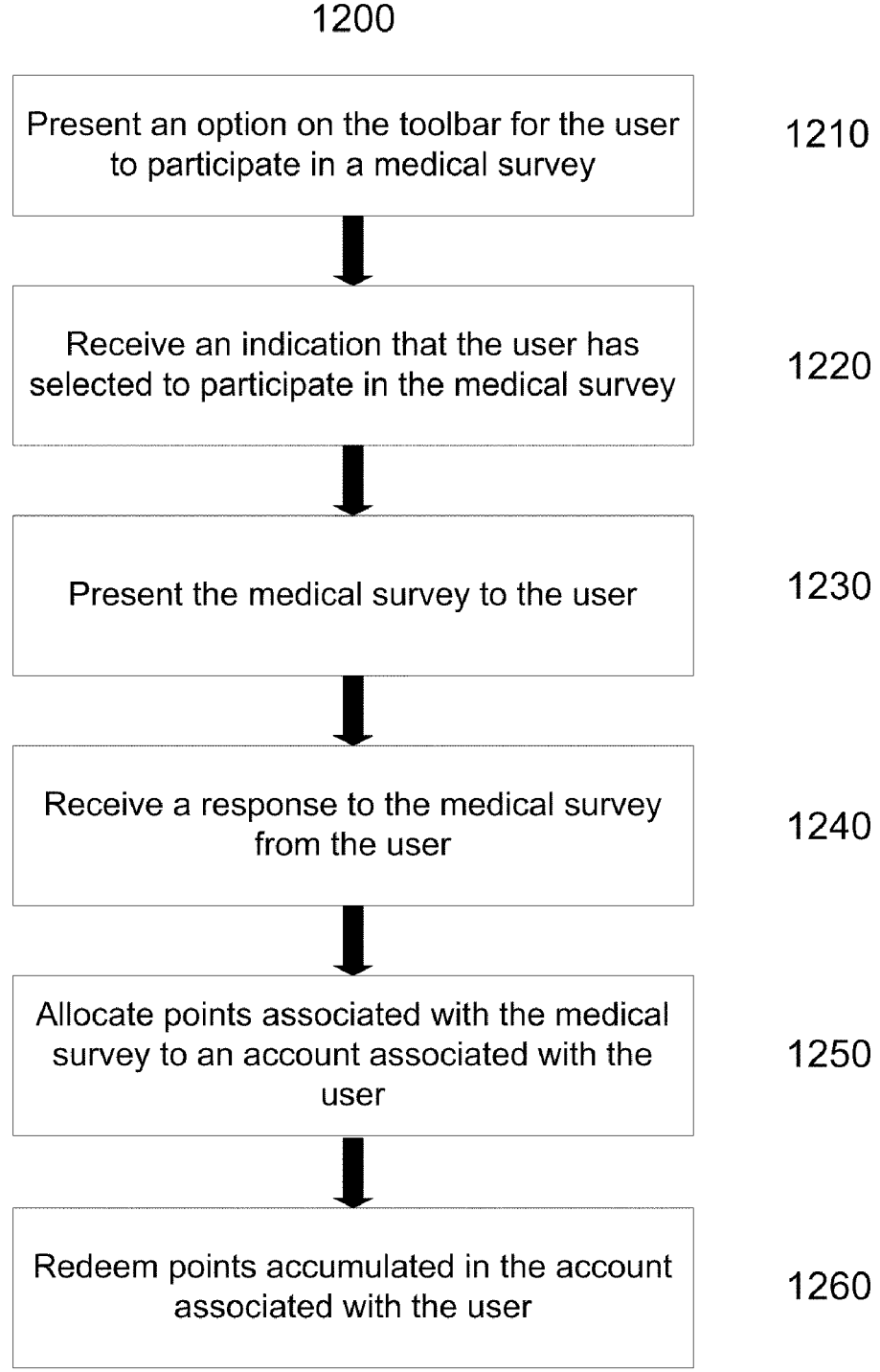
FIG. 12 is a flowchart of an example of a process for administering medical surveys using a toolbar.

FIG. 12 illustrates a flow diagram of a process 1200 to administer medical surveys using a toolbar. First, an option, such as button 424 of toolbar 410, is presented to a user to participate in a medical survey (step 1210). In one example, button 424 may be selectable when survey data structure 1400 includes survey identifiers 1420 associated with the user identifier in field 1410. If there are no survey identifiers 1420 associated with the user identifier in the survey data structure 1400, the text of button 424 may be changed to the color gray to indicate that button 424 is not selectable.

If button 424 is selectable and the user selects, by clicking on, button 424, a host, such as the host system 250, will receive an indication that the user has selected to participate in the medical survey (step 1220) and will present the medical survey to the user (step 1230). The user of the toolbar will be presented with a user interface to complete a medical survey, such as the user interface 160 of FIG. 1b. As illustrated in FIG. 1b, survey web page 160 includes survey questions 170, a button 180 selectable by the user to submit responses to the survey questions, and a button 190 selectable by the user to exit the survey web page 160. The survey questions may be stored in a separate survey file associated with survey data structure 1300. After the user selects button 424, the survey file for the survey to be completed is accessed and used to generate the survey web page 160.

Alternatively, the user may be presented with a list of uncompleted surveys retrieved from survey data structure 1300. The user selects one of the presented uncompleted surveys. In this example, after the user selects button 424, the survey data structure 1300 is accessed and all instances of the user identifier associated with the user are retrieved. Next, the survey identifiers 1320, survey names 1330, and points associated with each survey 1340 are identified for each survey associated with the user identifier. For example, as illustrated in FIG. 13, user identifier "1" is associated with survey identifiers "110" and "120." The survey names 1330 and the points associated with each survey 1340 identified will be presented to the user so that the user can select a survey of interest to complete.

The surveys associated with a user in the survey data structure 1300 may be based on information provided by the user in the user's user profile or based on past survey answers provided by the user. For example, if the user has identified himself as a radiologist, the user may be presented surveys related to x-rays systems. In another example, if the user has indicated a high interest in college education funding, surveys related to financial services may be presented to the user.

The points associated with each survey may be assigned by an administrator of the survey or by the administrator of the toolbar system. The point value associated with each survey may differ based on the number of questions in the survey or based on the type of information being acquired from the user. For example, information about the user's occupation may be associated with a greater number of points than information associated with the user's interests.

The responses to the survey questions may be completed by the user using radio buttons, selectable boxes, or data entry blocks. In one example, responses to some survey questions, such as demographic information of the user, may be automatically completed without user intervention based of the user's profile or previous responses to survey questions. This feature will save the user time in completing surveys and will encourage the user to complete more surveys.

After the user completes the survey questions 170 and selects button 180 to submit the responses to the medical survey questions, the host receives the responses (step 1240). The responses may be stored in a separate file associated with the user or in a field of survey data structure 1300 (not shown). The dates that the user completes the surveys are stored in field 1350 of survey data structure 1300.

Next, points associated with the survey are allocated to an account associated with the user (step 1250) and the dates of the allocation of the points are stored in field 1360. Typically, the points associated with a survey will be allocated to an account associated with the user on the same date the survey is completed by the user. However, if the responses to the survey must first be verified, then the points may be allocated to the account associated with the user at a later date.

Field 1370 of the survey data structure 1300 stores the expiration date of the points associated with each survey. In another example, the survey data structure 1300 may not include field 1370 as the expiration date may be a predetermined time period from the date which the user completed the survey or the date which the points were allocated to the user's account. The predetermined time period for expiration may be different for each survey or may be the same.

To determine a total number of points in the user's account, to be presented as an indication 426 on the toolbar 410, the sum of all of the point in field 1340 is calculated. However, if the expiration date of the points associated with a completed survey has elapsed, the points associated with that survey are not included in the total number of points in the user's account. In one example, the total number of points in the user's account may be updated after a user completes a survey. In another example, the total number of points in the user's account may also be updated at predetermined time intervals, such as once every hour or once every day.

Finally, the user may redeem the points accumulated in a user's account (step 1260) by selecting, by clicking on, indication 426. Selection of indication 426 results in presentation of a web page, such as the web page 1405 in FIG. 14, or in sending an e-mail including information on redeeming points to the user.

FIG. 14 is an example of a redemption user interface 1400 that enables a user of the toolbar to redeem points accumulated in the user's account for completing surveys. The redemption user interface 1400 includes web page 1405. Web page 1405 includes item identifiers 1410, items names 1420, item prices 1430, points required to acquire the items 1440, expiration dates associated with the items 1450, and selectable links 1450 to acquire the items.

The item identifiers 1410 and item names 1420 both serve to identify the items. In one example, web page 1405 may not include item identifiers 1410. Item prices 1430 include a price associated with the item, such as a manufacturer's suggested retail price (MSRP). In another example, the web page 1405 may not include item prices. Points required to acquire the items 1440 identifies the point that will be deducted from the user's account to acquire the item. Expiration dates associated with the items 1450 identifies a final date which the user can acquire the item. In one example, some items may not have an expiration date, whereas others each have different expiration dates. The selectable links 1450 may be selected by the user of the toolbar 710 to acquire one or more of the items.

In another example, points may be redeemed for gift certifications to various stores. Gift certificates of various denominations will each be associated with a different number of points required to acquire the gift certificates.

Various modifications may be made. For example, rather than being an element of a web browser, the toolbar 110 and 710 may be implemented on the desktop of a personal computer, Personal Digital Assistant (PDA), mobile phone, or other portable device.

A tangible computer-readable medium may be a physical medium that can be read by a computer such as, but not limited to, a computer storage device or an optical disc. The tangible computer-readable medium may be part of the client system 240 or the host system 250.

In another example, if multiple adverse events are reported in a medical study, notification messages associated with the adverse event may be presented in blocks 120 and 720 sequentially in the order they are received from the participants of the medical study or in the order in which the adverse events occurred. In another example, the notification messages may be presented in order of severity, such that the notification message associated with a more severe adverse event is presented in blocks 120 and 720 before the notification message associated with a less severe adverse event. If two or more adverse events sharing the same level of severity are to be presented in blocks 120 and 720, the notification messages for those adverse events are selected in the order in which the adverse events were submitted or occurred.

In yet another example, a notification message of a single adverse event is repeatedly presented in blocks 120 and 720 until the participant of the medical study acknowledges, if necessary, the adverse event. Once the participant acknowledges the adverse event, a notification message of another adverse event may be presented to the participant.

The participant of the medical study and/or the user of the toolbar may include, for example, the administrator of the medical study, a physician conducting the trials of the medical study, or a patient undergoing treatment.

The toolbar 110 and 710 may also be used to notify users of the toolbar, such as patients, of upcoming appointments and/or to take their medications. In one example, the administrator of the medical study may provide an appointment schedule or timeline and/or medication schedule or timeline using host device 252. The patient's client device 242 receives the appointment schedule and/or medication schedule from the host device 252, and displays a notification message alerting the patient of an upcoming appointment or time to take a medication on toolbar 110 and 710. The patient can acknowledge perception of the notification using the same mechanisms used to acknowledge perception of the description of an adverse event occurring in the medical study as explained above.

In another example, a patient can enter the appointment schedule and/or medication schedule at the client device 242. In this example, the toolbar 110 and 710 would use the appointment schedule and/or medication schedule provided by the patient to display a notification message alerting the patient of an upcoming appointment or time to take a medication.

A first notification of an appointment or first notification to take a medication will be displayed in block 720 of toolbar 710, similar to a notification of an insignificant adverse event. However, if the patient misses or does not acknowledge an appointment or a medication a threshold number of times, then the notification will be displayed in block 120 of toolbar 110, similar to a notifications of a serious adverse event. The threshold number of times a patient must miss or not acknowledge an appointment may be different than the threshold number of times the patient must miss or not acknowledge taking a medication.

For example, if the patient misses an appointment with a physician one time, subsequent notifications of that appointment will be displayed in block 120 of toolbar 110. However, if the patient misses taking a medication three times, subsequent notifications of the appointment will be displayed in block 120 of toolbar 110. A physician or administrator may provide indications that the patient has missed an appointment or a medication.

Alternatively, if the patient does not acknowledge the first two notifications of an appointment, subsequent notifications of that appointment will be displayed in block 120 of toolbar 110. In addition, the first three notifications to take a medication may be displayed in block 720 of toolbar 710. However, if the patient fails to acknowledge any of the first three notifications, subsequent notifications to take the medication will be displayed in block 120 of toolbar 110.

In one example, a physician, administrator, or patient provides an appointment schedule and/or a medication schedule by individually identifying every appointment and/or medication date and time. In another example, the physician, administrator, or patient is provided with a customizable or otherwise limited timeline associated with a particular medical study or medication. A customizable timeline is beneficial for medical studies with numerous patients, as appointment schedules and/or medication schedules can be generated for each of the patients quickly. In this example, a timeline for a cancer study may require that medication X be taken at noon everyday and that the patient visit the physician every Monday. An appointment schedule and medication schedule for a particular cancer patient may be generated based on the template cancer study timeline only by providing the start date for the patient in the medical study. In addition, the time to take the medication everyday and/or day to see the physician every week may be changed.

In another example of a timeline associated with the treatment of HIV using medication Y, the treatment duration is six months, medication Y is required three times a day, patient is required to see the physician every other month, the patient may requires blood work once a week, and patient requires X-rays once a month. A template timeline with those appointment and medication requirements may be created and individually customized by the physician, administrator, or patient for each patient undergoing treatment of HIV with medication Y.

In addition, points can be awarded to patients who timely acknowledge appointments and taking of medications. Points may be awarded to the patients using the same mechanisms used to award points for completing medical surveys explained above. The points awarded for acknowledging appointments and taking of medications may be combined with the points awarded for completing medical surveys or may be stored in a separate account for the patient. If the points awarded for acknowledging appointments and taking of medications are stored in a separate account, the points may be redeemed using the same mechanisms used to redeem points for completing medical surveys.

What is claimed is:

1. A tangible computer-readable medium having embodied thereon a user interface configured to disseminate information regarding an adverse event that has occurred in a medical study, the user interface comprising:
    a toolbar having:
    a first interface element structured and arranged to display at least one button associated with a first webpage in a first area of the toolbar in a first mode of the user interface and to not display the at least one button associated with the first webpage in a second mode of the user interface, the at least one button being selectable, in the first mode, by a user perceiving the user interface to inspire display of the first webpage; and
    a second interface element structured and arranged to display a description of an adverse event that has occurred in a medical study, the second interface element being selectable by the user perceiving the user interface to inspire display of a second webpage including a detailed description of the adverse event that has occurred in the medical study, the second webpage being different that the first webpage, and the second interface element being structured and arranged to set the user interface to the first mode upon selection of the second interface element,
    wherein the second interface element has, in the second mode, a first size to display a description of a relatively serious adverse event in a second area on the toolbar that includes the first area, and has, in the first mode, a second size to display a description of a relatively insignificant adverse event in a third area on the toolbar that does not include the first area and is included in the second area, the first size being greater than the second size, and
    wherein the first interface element is not displayed during display of the description of the relatively serious adverse event, and wherein the first interface element is displayed after the second interface element is selected and the second webpage is displayed.

2. The medium of claim 1, wherein the relatively serious adverse event comprises an adverse event that has a severity greater than a predetermined threshold.

3. The medium of claim 1, wherein the second interface element is structured and arranged to display a description of an adverse event according to one or more text properties, the text properties for displaying a description of the relatively serious adverse event being different that the text properties for displaying a description of the relatively insignificant adverse event.

4. A computer-implemented method for disseminating, on a toolbar, information regarding an adverse event that has occurred in a medical study, the method comprising:
    receiving an identifier of the medical study;
    identifying, based on the identifier of the medical study by at least one computer processor, participants of the medical study to whom information regarding the adverse event will be disseminated;
    receiving a description of a relatively insignificant adverse event that has occurred in the medical study;
    enabling presentation, to the participants of the medical study by at least one computer processor in a first mode, of a first interface element, the first interface element including the description of the relatively insignificant adverse event and that is selectable by a user to inspire display of a first webpage and a second interface element that includes at least one button that is selectable by a user to inspire display of a second webpage, the description of the relatively insignificant adverse event being presented in a first area of the toolbar in the first mode and the button being presented in a different second area of the toolbar;
    receiving a description of a relatively serious adverse event that has occurred in the medical study, wherein the severity of the relatively serious adverse event is greater relative to the severity of the insignificant adverse event, and wherein receiving the description of the relatively serious adverse event occurring in the medical study comprises:
        receiving an indication that the relatively serious adverse event is serious;
        receiving a notification message regarding the relatively serious adverse event to be presented to the participants of the medical study; and
        receiving a detailed description of the relatively serious adverse event to be presented to the participants of the medical study;
    setting the toolbar to a second mode in response to receiving the indication that the relatively serious adverse event is serious;
    enabling presentation, to the participants of the medical study by at least one computer processor in the second mode, of the first interface element, the first interface element including the description of the relatively serious adverse event, the first interface element being selectable by a user to inspire display of the first webpage and to set the toolbar to the first mode, and the first interface element being presented in a third area of the toolbar, the third area including the first area and the second area,
    requiring, in response to receiving the indication that the relatively serious adverse event is serious, that a particular participant of the medical study acknowledge their perception of the description of the adverse event; and
    receiving, from the particular participant of the medical study, an acknowledgement of their perception of the description of the relatively serious adverse event, wherein, after receiving the acknowledgement, the second interface element is displayed in the first area of the toolbar in the first mode.

5. The method of claim 4, wherein enabling presentation, to the participants of the medical study, of the description of the relatively insignificant adverse event comprises:
accessing a database to determine one or more text properties to be used for purposes of formatting a presented description of the relatively insignificant adverse event; and
enabling presentation, to the participants of the medical study, of the description of the relatively insignificant adverse event according to the determined one or more text properties, the description of the relatively insignificant adverse event being positioned on the toolbar with the at least one button.

6. The method of claim 5, wherein enabling presentation, to the participants of the medical study, of the description of the relatively serious adverse event comprises:
accessing a database to determine one or more text properties to be used for purposes of formatting a presented description of the relatively serious adverse event, wherein the one or more text properties for presenting the description of the relatively serious adverse event comprise at least one of text color, text size, an indication that the text will be flashing, and an indication that the text will be scrolling; and
enabling presentation, to the participants of the medical study, of the description of the relatively serious adverse event according to the determined one or more text properties, the description of the relatively serious adverse event being positioned on the toolbar,
wherein the one or more text properties for presenting the description of the relatively insignificant adverse event are different than the one or more text properties for presenting the description of the relatively serious adverse event.

7. The method of claim 4, wherein the relatively serious adverse event comprises an adverse event that affects patients in the medical study in a life threatening manner.

8. The method of claim 4, wherein receiving, from the particular participant of the medical study, an acknowledgement of their perception of the description of the relatively serious adverse event comprises:
receiving, from the particular participant of the medical study, an indication of their perception of the description of the relatively serious adverse event; and
receiving, from the particular participant of the medical study, a comment associated with the relatively serious adverse event.

9. The method of claim 4, wherein receiving, from the particular participant of the medical study, the acknowledgement of their perception of the description of the relatively serious adverse event comprises receiving, from the particular participant of the medical study, an indication that the particular participant of the medical study will later acknowledge perception of the description of the relatively serious adverse event.

10. The method of claim 9, further comprising:
identifying a date of receiving the indication that the particular participant of the medical study will later acknowledge perception of the description of the relatively serious adverse event;
accessing, from a database, a predetermined time period for following up with the particular participant of the medical study that will later acknowledge perception of the description of the relatively serious adverse event; and
enabling presentation, to the particular participant of the medical study that will later acknowledge perception of the description of the relatively serious adverse event, of a notification requesting acknowledgement of their perception of the description of the relatively serious adverse event after a predetermined time period.

11. The method of claim 9, further comprising:
determining which of the participants of the medical study have not acknowledged perception of the description of the relatively serious adverse event; and
enabling presentation, to the participants of the medical study have not acknowledged perception of the description of the relatively serious adverse event, of a notification requesting acknowledgement of perception of the description of the relatively serious adverse event.

12. The method of claim 4, wherein the toolbar is an element of a web browser that is perceptible by a user of the web browser.

13. The method of claim 4, wherein identifying, based on the identifier of the medical study, the participants of the medical study to whom information regarding the adverse event will be disseminated comprises:
accessing a database storing identifiers of participants of one or more medical studies and identifiers of the one or more medical studies;
comparing the identifier of the medical study with the stored identifiers of the one or more medical studies;
determining that the identifier of the medical study is equal to one of the stored identifiers of the one or more medical studies; and
retrieving, based on the determination that the identifier of the medical study is equal to one of the stored identifiers of the one or more medical studies, identifiers of the participants of the medical study.

14. The method of claim 4, wherein receiving, from the particular participant of the medical study, the acknowledgement of their perception of the description of the relatively serious adverse event comprises:
receiving an indication that the particular participant has selected the description of the relatively serious adverse event positioned on the toolbar; and
enabling presentation, to the particular participant and in response to receiving the indication that the particular participant has selected the description of the relatively serious adverse event, of a web page including a selectable button enabling acknowledgement of perception of the description of the relatively serious adverse event.

* * * * *